United States Patent
Yamashita et al.

(10) Patent No.: US 9,816,975 B2
(45) Date of Patent: Nov. 14, 2017

(54) FLUID STATE DETECTION APPARATUS

(71) Applicant: NGK SPARK PLUG CO., LTD., Nagoya-shi, Aichi (JP)

(72) Inventors: Masahiro Yamashita, Komaki (JP); Shoji Kitanoya, Kasugai (JP); Masaya Watanabe, Komaki (JP)

(73) Assignee: NGK SPARK PLUG CO., LTD., Aichi (JP)

(*) Notice: Subject to any disclaimer, the term of this patent is extended or adjusted under 35 U.S.C. 154(b) by 45 days.

(21) Appl. No.: 15/090,751

(22) Filed: Apr. 5, 2016

(65) Prior Publication Data

US 2016/0299094 A1 Oct. 13, 2016

(30) Foreign Application Priority Data

Apr. 8, 2015 (JP) .................................. 2015-079442

(51) Int. Cl.
*G01N 33/00* (2006.01)
*G01N 27/12* (2006.01)
*G01N 27/14* (2006.01)

(52) U.S. Cl.
CPC ....... *G01N 33/0036* (2013.01); *G01N 27/123* (2013.01)

(58) Field of Classification Search
CPC .. G01N 33/0036; G01N 27/123; G01N 27/04; G01N 27/14
See application file for complete search history.

(56) References Cited

U.S. PATENT DOCUMENTS 2,971,137 A * 2/1961 Stewart, Jr. ........ G05D 23/2453
219/499
6,752,014 B1 * 6/2004 Kanke ................... G01F 1/6845
73/204.15

FOREIGN PATENT DOCUMENTS

| JP | 2012-198093 A | 10/2012 |
| JP | 2012198093 A * | 10/2012 |
| JP | 2012198751 A * | 10/2012 |

* cited by examiner

*Primary Examiner* — Michele Fan
(74) *Attorney, Agent, or Firm* — Sughrue Mion, PLLC

(57) ABSTRACT

A fluid state detection apparatus which can detect a short failure in which a constituent Wheatstone bridge circuit is shorted to a power supply. A combustible gas detection apparatus (1) judges that a short failure has occurred in a constant temperature control circuit (231) (S240) when a top potential V21 is equal to or greater than a first judgment value Vth1 and a difference D1 (=V11−V31) is equal to or greater than a second judgment value Vth2. As a result, apparatus (1) can distinguish "a state in which a bridge circuit (210) is shorted to a DC power supply (40) (where the constant temperature control circuit 231 is in a short failure state)" from "a state in which the resistance of the heat generation resistor (15) deceases due to a combustible gas (hydrogen)" based on the top potential V21 and the difference D1.

4 Claims, 5 Drawing Sheets

FLUID STATE DETECTION APPARATUS

BACKGROUND OF THE INVENTION

1. Field of the Invention

The present invention relates to a fluid state detection apparatus for detecting the state of a fluid within a target atmosphere.

2. Description of the Related Art

Fluid state detection apparatuses have been used to detect the state of a fluid (concentration of gas, flow rate of gas, flow rate of liquid, temperature, or the like) within a target atmosphere.

A known fluid state detection apparatus for detecting the state of a fluid within a target atmosphere includes a heat generation resistor whose resistance changes with the fluid state to be detected. This fluid state detection apparatus measures, for example, the amount of heat transferred from the heat generation resistor to the fluid to be detected and calculates a change in the heat conduction of the fluid to be detected. In this manner, the fluid state detection apparatus can detect the fluid state (for example, hydrogen concentration, etc.).

A fluid state detection apparatus has been known which is configured to measure the amount of heat transferred from a heat generation resistor to a fluid to be detected using a Wheatstone bridge circuit (hereinafter also referred to as a "bridge circuit") which includes the heat generation resistor as one of four resistor sections.

In the case of a fluid state detection apparatus in which such a bridge circuit is used, an open failure may occur in which the connection between the bridge circuit and the inverting input terminal of an operational amplifier is broken, or an open failure in which the connection to the output terminal of the operational amplifier is broken.

In view of the above, a fluid state detection apparatus which detects such an open failure has been proposed (Patent Document 1). In the proposed fluid state detection apparatus, the resistance of each of the individual resistor sections of the bridge circuit is properly set such that when the above-mentioned open failure occurs, the output of the operational amplifier deviates from its normal output range, whereby the fluid state detection apparatus can detect the open failure.

Incidentally, in recent years, in consideration of environmental protection and nature conservation among other societal demands, research has been actively conducted on fuel cells, which are energy sources of high efficiency and low environmental load. Among various types of fuel cells, a polymer electrolyte fuel cell (PEFC) has drawn attention as an energy source for home use or an energy source for vehicles because of its advantageous low operation temperature and high output density. Such a polymer electrolyte fuel cell uses, as a fuel, hydrogen which is more likely to leak as compared with other fuels. Therefore, a fluid state detection apparatus which detects hydrogen leakage has become necessary for practical implementation of a polymer electrolyte fuel cell.

Also, research has been actively conducted on a hydrogen internal combustion engine which is an energy source having a low environmental load and which uses hydrogen as a fuel similar to the polymer electrolyte fuel cell. As for the hydrogen internal combustion engine as well, a fluid state detection apparatus which detects hydrogen leakage has become necessary for practical implementation.

[Patent Document 1] Japanese Patent Application Laid-Open (kokai) No. 2012-198093

3. Problem to be Solved by the Invention

However, in the case of the above-described fluid state detection apparatus, when the bridge circuit is shorted to a power supply (for example, when a short failure has occurred in an energization control section which controls the supply of current from the power supply to the bridge circuit), detection of the short failure is difficult.

Namely, since the output of the operational amplifier at the time of the short failure (in which the bridge circuit is shorted to the power supply) remains within the normal output range of the operational amplifier, it is difficult to detect such a failure by the above-described method of properly setting the resistances of the resistor sections of the bridge circuit as described above.

For example, in the case where the resistance of the heat generation resistor decreases due to the fluid state to be detected, as a result of the feedback control performed by the operational amplifier, the current supplied from the energization control section to the bridge circuit is controlled to a maximum value (or the applied voltage is controlled to a maximum value). This is a control state created as a result of detecting the fluid state, and is a normal control state of the fluid state detection apparatus.

Meanwhile, when the energization control section (for example, a transistor) enters a short failure state and the bridge circuit is shorted to the power supply, the supply of current from the power supply to the bridge circuit cannot be controlled, whereby the current supplied to the bridge circuit assumes a maximum value (or the applied voltage assumes a maximum value). This is a state created as a result of a short failure of the energization control section, and is an anomaly state (failure state) of the fluid state detection apparatus.

As described above, the current supplied to the bridge circuit becomes a maximum (or the applied voltage becomes a maximum) and the output of the operational amplifier assumes the same value in both the normal state in which the resistance of the heat generation resistor decreases and a short failure state of the energization control section (in other words, when the bridge circuit is shorted to the power supply). Therefore, it is difficult to distinguish the two states from each other based on the output of the operational amplifier.

SUMMARY OF THE INVENTION

It is therefore an object of the present invention to provide a fluid state detection apparatus which can detect a short failure in the event that a Wheatstone bridge circuit, which is a component of the detection apparatus, is shorted to a power supply.

The above object has been achieved by providing (1) a fluid state detection apparatus which comprises a heat generation resistor, a Wheatstone bridge circuit, a bridge control section, and a computation section. The bridge control section includes an operational amplifier and an energization control section. Further, the fluid state detection apparatus comprises a failure judgment section.

The heat generation resistor is disposed in a target atmosphere, and its resistance changes in accordance with a fluid state to be detected. The Wheatstone bridge circuit is configured by connecting, in parallel, a first side including the heat generation resistor and a first resistor section connected in series, and a second side including a second resistor section and a third resistor section connected in series. The bridge control section controls a state of supply of electric current from a power supply to the Wheatstone bridge circuit. The computation section computes the fluid state within the target atmosphere based on the resistance of the heat generation resistor.

The operational amplifier has an output terminal and two input terminals. The energization control section controls the state of supply of electric current to the Wheatstone bridge circuit in accordance with the output of the operational amplifier such that a potential difference between the two input terminals of the operational amplifier becomes zero.

The Wheatstone bridge circuit is configured such that one of connection points where the first side and the second side are connected together serves as a reference point connected to one side of the bridge control section which becomes a low potential side when the bridge control section applies a voltage to the Wheatstone bridge circuit, and the other of the connection points serves as a high potential point connected to the other side of the bridge control section which becomes a high potential side when the bridge control section applies the voltage to the Wheatstone bridge circuit. Also, the Wheatstone bridge circuit is configured such that a connection point where the first resistor section and the heat generation resistor are connected together serves as a first potential point connected to one input terminal of the operational amplifier, and a connection point where the second resistor section and the third resistor section are connected together serves as a second potential point connected to the other input terminal of the operational amplifier.

The computation section may compute the fluid state within the target atmosphere using the voltage between opposite ends of the heat generation resistor which is detected based on at least the potential at the first potential point. Notably, since the voltage between the opposite ends of the heat generation resistor changes with the resistance of the heat generation resistor, it can be utilized as a state quantity corresponding to the resistance of the heat generation resistor.

The failure judgment section is configured to compare a potential at the high potential point with a predetermined voltage upper limit judgment value and to compare a difference obtained by subtracting a potential at the second potential point from a potential at the first potential point with a predetermined failure judgment value so as to judge whether or not the Wheatstone bridge circuit is in a short failure state in which it is shorted to the power supply (for example, when a failure has occurred in the energization control section). Specifically, the failure judgment section judges that the Wheatstone bridge circuit is in a short failure state in which it is shorted to the power supply when the potential at the high potential point is equal to or greater than the voltage upper limit judgment value and the difference is equal to or greater than the failure judgment value.

The voltage upper limit judgment value is determined based on the potential (potential at the time of maximum energization) produced at the high potential point when the state of control by the bridge control section is a state in which the maximum current is supplied from the power supply to the Wheatstone bridge circuit (or a state in which the maximum voltage is applied to the Wheatstone bridge circuit). For example, a value equal to or slightly smaller than the potential at the time of maximum energization is set as the voltage upper limit judgment value in advance.

An arbitrary value within the numerical range which ranges from the value of the difference at the time when the Wheatstone bridge circuit is in a short failure state in which it is shorted to the power supply to the value of the difference at the time when the resistance of the heat generation resistor decreases due to the fluid state to be detected is set as the failure judgment value in advance.

In the fluid state detection apparatus, when the Wheatstone bridge circuit is in a short failure state in which it is shorted to the power supply, the output voltage of the power supply is applied directly to the Wheatstone bridge circuit. When the application of such a voltage to the heat generation resistor continues, the temperature of the heat generation resistor increases, and the resistance of the heat generation resistor increases, whereby the voltage between the opposite ends of the heat generation resistor increases. Notably, the first resistor section, the second resistor section, and the third resistor section, which are provided as reference resistors of the Wheatstone bridge circuit, are smaller in resistance change with temperature change as compared with the heat generation resistor. Therefore, when the voltage between the opposite ends of the heat generation resistor increases, the potential at the first potential point becomes more apt to be higher than that at the second potential point.

Meanwhile, in the fluid state detection apparatus, when a state continues in which the resistance of the heat generation resistor decreases due to the fluid state to be detected, in order to increase the resistance of the heat generation resistor, the bridge control section controls the state of supply of electric current from the power supply to the Wheatstone bridge circuit such that the maximum current is supplied to the Wheatstone bridge circuit (or the maximum voltage is applied to the Wheatstone bridge circuit). At that time, since the resistance of the heat generation resistor decreases due to the fluid state to be detected, the voltage between the opposite ends of the heat generation resistor decreases. As a result of the decrease in voltage between opposite ends of the heat generation resistor, the potential at the first potential point becomes more apt to be lower than that at the second potential point.

Therefore, the difference obtained by subtracting the potential at the second potential point from the potential at the first potential point assumes different values between the "state in which the Wheatstone bridge circuit is in a short failure state in which it is shorted to the power supply" and the "state in which the resistance of the heat generation resistor decreases due to the fluid state to be detected." Therefore, in the case where the failure judgment value is set as described above and the result of the comparison between the difference and the failure judgment value is used, it becomes possible to distinguish the "state in which the Wheatstone bridge circuit is in a short failure state in which it is shorted to the power supply" from the "state in which the resistance of the heat generation resistor decreases due to the fluid state to be detected."

Notably, the difference obtained by subtracting the potential at the second potential point from the potential at the first potential point changes even when the energization control section is normal. Therefore, in addition to the difference, the potential at the high potential point is used for making the judgment. Thus, it is possible to judge whether or not the energization control section is in the short failure state.

By virtue of these, in "the case where the potential at the high potential point is equal to or greater than the voltage upper limit judgment value and the difference is equal to or greater than the failure judgment value," it is possible to judge that the Wheatstone bridge circuit is in a short failure state in which it is shorted to the power supply. Also, in "the case where the potential at the high potential point is equal to or greater than the voltage upper limit judgment value and the difference is neither equal to nor greater than the failure judgment value," it is possible to judge that the current state is a state in which the resistance of the heat generation resistor decreases due to the fluid state to be detected.

Therefore, by providing the above-described failure judgment section, the fluid state detection apparatus can distinguish the state in which the Wheatstone bridge circuit is shorted to the power supply (short failure state) from the state in which the resistance of the heat generation resistor has decreased due to the fluid state to be detected.

Accordingly, this fluid state detection apparatus can detect a short failure in which the Wheatstone bridge circuit is shorted to the power supply.

Notably, in the fluid state detection apparatus, when the failure judgment section judges that the potential at the high potential point is lower than the voltage upper limit judgment value or judges that the difference is smaller than the failure judgment value, the computation section computes the fluid state, whereby the fluid state can be detected.

Also, in the case where the failure judgment section judges that the potential at the high potential point is equal to or lower than the voltage upper limit judgment value and judges that the difference is smaller than the failure judgment value, the fluid state detection apparatus may judge that the current state is a state in which the resistance of the heat generation resistor has decreased due to the fluid state to be detected, and the computation section may compute the fluid state within the target atmosphere to thereby detect the fluid state.

In a preferred embodiment (2) of the above-described fluid state detection apparatus (1), the computation section computes hydrogen gas concentration as the fluid state.

The state in which the hydrogen gas concentration to be detected becomes high is a state in which the resistance of the heat generation resistor decreases. Therefore, when this state continues, in order to increase the resistance of the heat generation resistor, the bridge control section controls the state of supply of electric current from the power supply to the Wheatstone bridge circuit such that the maximum current is supplied to the Wheatstone bridge circuit (or the maximum voltage is applied to the Wheatstone bridge circuit).

Therefore, by providing the above-described failure judgment section, the fluid state detection apparatus can distinguish the state in which the Wheatstone bridge circuit is shorted to the power supply (short failure state) from the state in which the hydrogen gas concentration to be detected is high.

Accordingly, in the case where the present fluid state detection apparatus is used for detecting hydrogen gas concentration, the fluid state detection apparatus can detect a short failure in which the Wheatstone bridge circuit is shorted to the power supply.

Notably, in the case where the failure judgment section judges that the potential at the high potential point is equal to or lower than the voltage upper limit judgment value and judges that the difference is smaller than the failure judgment value, the fluid state detection apparatus may judge that the hydrogen concentration is high, and the computation section may compute the hydrogen concentration within the target atmosphere, to thereby detect the hydrogen concentration.

In another preferred embodiment (3) of the above-described fluid state detection apparatus (1) or (2), the power supply is integrated into the fluid state detection apparatus.

Examples of the form of connection between the fluid state detection apparatus and the power supply include a form in which the fluid state detection apparatus is connected to a power supply provided externally, and a form in which the fluid state detection apparatus is connected to a power supply that is integrally incorporated into the fluid state detection apparatus. In the case where the power supply is integrally provided in the fluid state detection apparatus, the Wheatstone bridge circuit is always connected to the power supply through the bridge control section (energization control section). Therefore, it is difficult to check the connection state and may be difficult to find a short anomaly.

In the case where the above-described failure judgment section is used for the fluid state detection apparatus having such a configuration in order to judge whether or not the Wheatstone bridge circuit is shorted to the power supply, it becomes possible to detect a short failure in which the Wheatstone bridge circuit is shorted to the power supply.

Effect of the Invention

The fluid state detection apparatus of the present invention can detect a short failure of the energization control section which controls the current supplied to the Wheatstone bridge circuit.

DESCRIPTION OF REFERENCE NUMERALS

Figure 1:
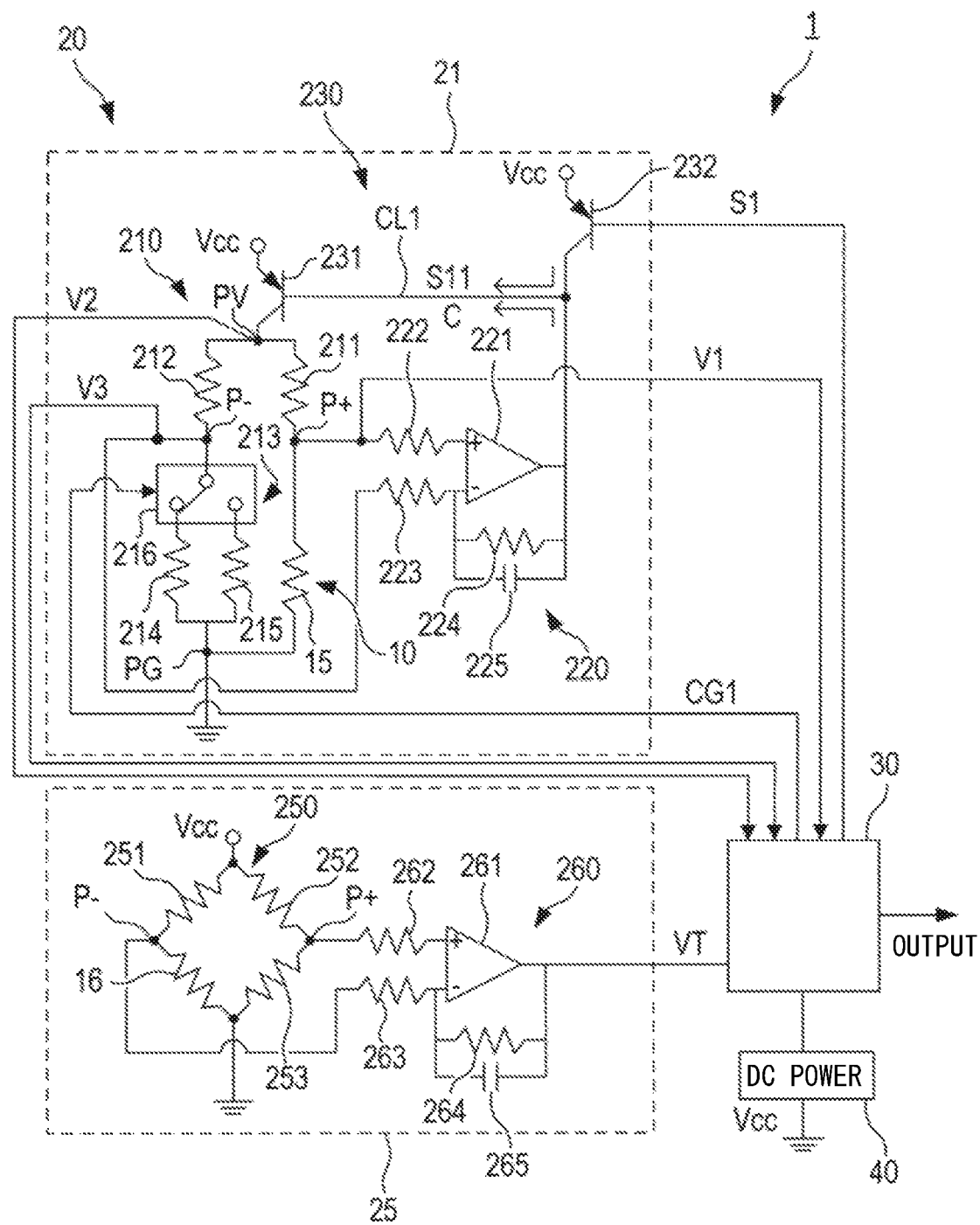
FIG. 1 is a diagram describing the overall configuration of a combustible gas detection apparatus.

Reference numerals used to identify various features in the drawings include the following.

1 . . . combustible gas detection apparatus, 10 . . . gas detection element, 15 . . . heat generation resistor, 16 . . . temperature measurement resistor, 20 . . . control section, 21 . . . energization control circuit, 25 . . . temperature adjustment circuit, 30 . . . computation section, 40 . . . DC power supply, 210 . . . bridge circuit, 211 . . . first bridge fixed resistor, 212 . . . second bridge fixed resistor, 213 . . . variable resistor section, 220 . . . amplification circuit, 221 . . . operational amplifier, 230 . . . current adjustment circuit, 231 . . . constant temperature control circuit.

DETAILED DESCRIPTION OF THE PREFERRED EMBODIMENTS

The present invention will now be described in greater detail with reference to the drawings. However, the invention should not be construed as being limited thereto.

1. First Embodiment

1-1. Overall Configuration

A combustible gas detection apparatus 1 which detects the concentration of hydrogen gas which is a combustible gas contained in a target atmosphere will be described as a first embodiment.

The combustible gas detection apparatus 1 is a heat-conduction-type gas detector, and is disposed in, for example, the cabin of an automobile powered by a fuel cell for the purpose of, for example, detecting hydrogen leakage. The combustible gas detection apparatus 1 transmits the detected gas concentration to an external device (for example, an engine control unit, etc.).

FIG. 1 is a diagram describing the overall configuration of the combustible gas detection apparatus 1.

The combustible gas detection apparatus 1 is mainly composed of a gas detection element 10 for detecting the concentration of hydrogen gas; a control section 20 for controlling the gas detection element 10; a computation section 30 for executing at least processing of computing the concentration of hydrogen gas based on an output signal of the gas detection element 10; and a DC power supply 40 for supplying electric power to the control section 20 and the computation section 30.

The DC power supply 40 supplies a drive voltage Vcc (5 V) to various portions of the combustible gas detection apparatus 1.

Figure 2A:
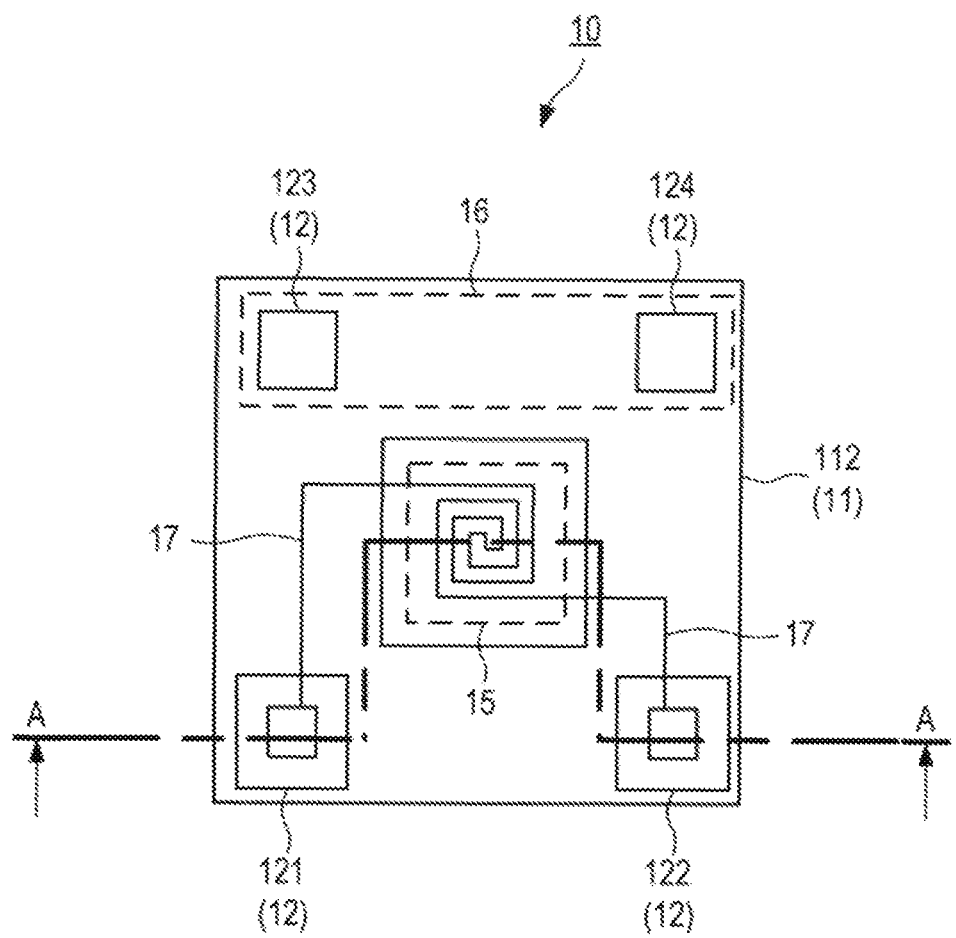
FIG. 2A and FIG. 2B are views illustrating the structure of a gas detection element.
Figure 2B:
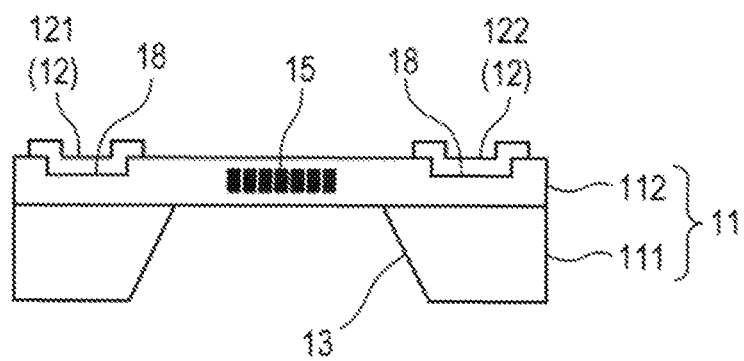

As shown in a plan view of FIG. 2A and a cross sectional view of FIG. 2B taken along A-A line of FIG. 2A, the gas detection element 10 mainly includes a base 11 formed into the shape of a flat plate; a plurality of electrodes 12 disposed on one surface (hereinafter referred to as the "front surface") of the base 11; and a recess 13 formed on the other surface (hereinafter referred to as the "back surface") of the base 11.

The base 11 constitutes the main body of the gas detection element 10 and is a rectangular plate member mainly formed of silicon. The base 11 is a rectangular plate member having a size of several millimeters in length and width (in the present embodiment, a size of about 3 mm×3 mm). An example of a technique for forming the plurality of electrodes and the recess 13 on the base 11 is a micromachining technique (micromachining process) performed for silicon substrates.

The base 11 is composed of a silicon substrate 111 mainly formed of silicon and an insulating layer 112 formed on the front surface of the silicon substrate 111. At the center of the silicon substrate 111, the silicon substrate 111 is removed to form the recess 13 having a square shape in plan view. On the back surface side of the silicon substrate 111, the insulating layer 112 is exposed through the recess 13. In other words, the base 11 is formed to have a diaphragm structure in which the silicon substrate 111 serves as a frame and the insulating layer 112 serves a membrane.

In a region of the insulating layer 112 corresponding to the recess 13, a line-shaped heat generation resistor 15 is embedded to form a spiral shape. In a region of a peripheral edge portion of the insulating layer 112 located on the upper side in FIG. 2A, a temperature measurement resistor 16 for measuring the temperature of the target atmosphere is embedded.

Since the base 11 has the above-described recess 13, a space is formed below a portion of the insulating layer 112 where the heat generation resistor 15 is provided. As a result, the heat generation resistor 15 is thermally isolated from the surroundings (the silicon substrate 111, etc.). Therefore, the temperature of the heat generation resistor 15 can be increased or decreased within a short period of time, whereby the electric power consumed by the heat generation resistor 15 can be reduced.

Notably, the insulating layer 112 may be formed of a single material or formed through use of different materials to have a multi-layer structure. Examples of an insulating material used to form the insulating layer 112 include silicon oxide ($SiO_2$) and silicon nitride ($Si_3N_4$).

The heat generation resistor 15 is formed of an electrically conductive material whose resistance changes with a change in temperature (of the resistor itself) and which has a large temperature coefficient of resistance. The temperature measurement resistor 16 is formed of an electrically conductive material whose electric resistance changes in proportion to the temperature. In the present embodiment, the temperature measurement resistor 16 is formed of an electrically conductive material whose resistance increases as the temperature rises.

The heat generation resistor 15 and the temperature measurement resistor 16 may be formed of the same material. In the present embodiment, the heat generation resistor 15 and the temperature measurement resistor 16 are formed of platinum (Pt).

When the resistance of the temperature measurement resistor 16 changes with the temperature in a state in which a constant current is supplied thereto, the voltage between opposite ends of the temperature measurement resistor 16 (the potential difference between the opposite ends) changes. A voltage obtained by amplifying the voltage between opposite ends of the temperature measurement resistor 16 is output as a temperature detection signal VT which will be described below. This temperature detection signal VT assumes a reference value (a predetermined potential difference) when the temperature of the target atmosphere to which the gas detection element 10 is exposed is a reference temperature set in advance.

The electrodes 12 are four electrodes formed on the front surface of the base 11 at respective positions near the four apexes of the rectangle, and are formed of, for example, aluminum (Al) or gold (Au). Of the electrodes 12, two electrodes disposed at the two apexes on the lower side in FIG. 2A are a first electrode 121 and a first ground electrode 122, and two electrodes disposed at the two apexes on the upper side in FIG. 2A are a second electrode 123 and a second ground electrode 124.

Notably, the first electrode 121 is connected to a connection point P+ of an energization control circuit 21 which will be described below, and the second electrode 123 is connected to a connection point P− of a temperature adjustment circuit 25 which will be described below. Both the first ground electrode 122 and the second ground electrode 124 are connected to a ground line which is shared by the control section 20.

Wiring lines 17 and wiring films 18 are provided in the base 11 (specifically, in the insulating layer 112). The wiring lines 17 and the wiring films 18 electrically connect the heat generation resistor 15 to the first electrode 121 and the first ground electrode 122. The first electrode 121 and the first ground electrode 122 formed on the front surface of the base 11 are electrically connected to the wiring films 18 formed in the insulating layer 112 through electrically conductive contact holes. In other words, the heat generation resistor 15 is electrically connected to the first electrode 121 at one end, and is electrically connected to the first ground electrode 122 at the other end.

Notably, the same material as the material used to form the heat generation resistor 15 may be used to form the wiring lines 17 and the wiring films 18.

Also, wiring films (not shown) for electrically connecting the temperature measurement resistor 16 to the second electrode 123 and the second ground electrode 124 are provided in the insulating layer 112. In other words, the temperature measurement resistor 16 is electrically connected to the second electrode 123 at one end and is electrically connected to the second ground electrode 124 at the other end.

Notably, the same material as the material used to form the temperature measurement resistor 16 may be used to form the wiring film for electrically connecting the temperature measurement resistor 16 and the second electrode 123, and to form the wiring film for electrically connecting the temperature measurement resistor 16 and the second ground electrode 124.

1-2. Control Section

Referring back to FIG. 1, the energization control circuit 21 and the temperature adjustment circuit 25 are provided in the control section 20.

The energization control circuit 21 controls the supply of electric current to the heat generation resistor 15. Also, the energization control circuit 21 outputs various signals (detection signal V1, TOP voltage signal V2, and intermediate potential signal V3) to the computation section 30. The detection signal V1 is a signal corresponding to the voltage between opposite ends (inter-terminal voltage) of the heat generation resistor 15. The TOP voltage signal V2 is a signal corresponding to the potential at a connection end portion PV where the first bridge fixed resistor 211 and the second bridge fixed resistor 212 are connected. The intermediate potential signal V3 is a signal corresponding to the potential at the connection point P− at which the second bridge fixed resistor 212 and the variable resistor section 213 are connected. Notably, the detection signal V1 also serves as a signal corresponding to the potential at the connection point P+ at which the first bridge fixed resistor 211 and the heat generation resistor 15 are connected.

The temperature adjustment circuit 25 supplies electric current to the temperature measurement resistor 16. Also, the temperature adjustment circuit 25 outputs a temperature detection signal VT regarding the temperature of the target atmosphere to the computation section 30.

Also, as will be described below, the potential at the connection point P+ between the first bridge fixed resistor 211 and the heat generation resistor 15 and the potential at the connection point P− between the second bridge fixed resistor 212 and the variable resistor section 213 are controlled by feedback control performed by an amplification circuit 220 and a current adjustment circuit 230 such that the two potentials become the same.

The energization control circuit 21 maintains the temperature of the heat generation resistor 15 at a predetermined temperature. The energization control circuit 21 includes a bridge circuit 210 which is a Wheatstone bridge circuit including the heat generation resistor 15; the amplification circuit 220 which amplifies the potential difference detected by the bridge circuit 210; and the current adjustment circuit 230 which adjusts (increases or decreases) the current flowing to the bridge circuit 210 in accordance with the output of the amplification circuit 220.

The bridge circuit 210 is a Wheatstone bridge circuit which includes the heat generation resistor 15, the first bridge fixed resistor 211, the second bridge fixed resistor 212, and the variable resistor section 213 whose resistance can be switched to a different resistance value. The bridge circuit 210 is composed of a first-side circuit and a second-side circuit which are connected in parallel to each other. The first-side circuit includes the heat generation resistor 15 and the first bridge fixed resistor 211 connected in series, and the second-side circuit includes the second bridge fixed resistor 212 and the variable resistor section 213 connected in series.

The first bridge fixed resistor 211 is connected in series to the heat generation resistor 15. Of end portions of the heat generation resistor 15, the end portion PG opposite the end portion connected to the first bridge fixed resistor 211 is grounded. Of end portions of the first bridge fixed resistor 211, the end portion PV connected to the second bridge fixed resistor 212 is connected to the current adjustment circuit 230 (specifically, a constant temperature control circuit 231). Notably, in the case where one end of the heat generation resistor 15 is connected to the reference point (ground), the potential at the one end of the heat generation resistor 15 becomes equal to the potential at the reference point. Therefore, the potential at the other end of the heat generation resistor 15 (the connection point P+ in the present embodiment) corresponds to the voltage between the opposite ends of the heat generation resistor 15.

Also, the second bridge fixed resistor 212 is connected in series to the variable resistor section 213. Of end portions of the variable resistor section 213, the end portion PG opposite the end portion connected to the second bridge fixed resistor 212 is grounded. Of end portions of the second bridge fixed resistor 212, the end portion PV connected to the first bridge fixed resistor 211 is connected to the current adjustment circuit 230 (specifically, the constant temperature control circuit 231).

The connection point P+ between the first bridge fixed resistor 211 and the heat generation resistor 15 is connected to the non-inverting input terminal of the operational amplifier 221 through a first fixed resistor 222. The potential at the connection point P+ is supplied to the computation section 30 as the detection signal V1. Also, the connection point P− between the second bridge fixed resistor 212 and the variable resistor section 213 is connected to the inverting input terminal of the operational amplifier 221 through a second fixed resistor 223. The potential at the connection point P− is supplied to the computation section 30 as the intermediate potential signal V3.

The variable resistor section 213 is configured such that the resistance of the variable resistor section 213 can be switched and is provided so as to change the balance of the bridge circuit 210. As shown in FIG. 1, the variable resistor section 213 includes a first fixed resistor 214, a second fixed resistor 215, and a changeover switch 216.

The first fixed resistor 214 and the second fixed resistor 215 are formed of resistor elements having different resistances. The changeover switch 216 connects one of the first fixed resistor 214 and the second fixed resistor 215 between the second bridge fixed resistor 212 and the heat generation resistor 15. The changeover switch 216 performs the switching operation in accordance with a changeover signal CG1 output from the computation section 30.

Notably, the first fixed resistor 214 has a resistance determined such that the temperature of the heat generation resistor 15 becomes a first set temperature CH (a high-temperature-side set temperature; for example, 400° C.). The second fixed resistor 215 has a resistance determined such that the temperature of the heat generation resistor 15 becomes a second set temperature CL (a low-temperature-side set temperature; for example, 300° C.) which is lower than the first set temperature CH.

Notably, the bridge circuit 210 is configured such that the set temperature of the heat generation resistor 15 can be switched to the first set temperature CH or the second set temperature CL by switching the resistance of the variable resistor section 213.

When the temperature of the heat generation resistor 15 is set to the first set temperature CH, the first fixed resistor 214 is connected between the second bridge fixed resistor 112 and the heat generation resistor 15 by the changeover switch 216. The voltage between the opposite ends of the heat generation resistor 15 at that time is a high-temperature-time voltage VH.

When the temperature of the heat generation resistor 15 is set to the second set temperature CL, the second fixed resistor 115 is connected between the second bridge fixed resistor 112 and the heat generation resistor 15 by the changeover switch 216. The voltage between the opposite ends of the heat generation resistor 15 at that time is a low-temperature-time voltage VL.

Notably, in the present embodiment, since the temperature difference between the first set temperature CH (the high-temperature-side set temperature) and the second set temperature CL (the low-temperature-side set temperature) is 100° C. or more, the resolution in the ratio between the high-temperature-time voltage VH and the low-temperature-time voltage VL can be increased. Namely, by accurately calculating the humidity H of the target atmosphere by setting the temperature difference between the first set temperature CH and the second set temperature CL to 50° C. or more, the resolution in the ratio between the high-temperature-time voltage VH and the low-temperature-time voltage VL can be increased.

As shown in FIG. 1, the amplification circuit 220 is a differential amplification circuit and includes the operational amplifier 221, the first fixed resistor 122, the second fixed resistor 123, a third fixed resistor 124, and a capacitor 225. The first fixed resistor 122 is connected between the non-inverting input terminal of the operational amplifier 221 and the connection point P+. The second fixed resistor 123 is connected between the inverting input terminal of the operational amplifier 221 and the connection point P−. The third fixed resistor 224 and the capacitor 225 are connected in parallel between the inverting input terminal of the operational amplifier 221 and the output terminal thereof.

The amplification circuit 220 operates as follows. In the case where the voltage input to the non-inverting input terminal of the operational amplifier 221 is larger than that input to the inverting input terminal of the operational amplifier 221, the amplification circuit 220 operates to increase the value of an adjustment signal C which is an output of the circuit. In the case where the voltage input to the non-inverting input terminal of the operational amplifier 221 is smaller than that input to the inverting input terminal of the operational amplifier 221, the amplification circuit 220 operates to decrease the value of an adjustment signal C.

The current adjustment circuit 230 (specifically, the constant temperature control circuit 231) increases or decreases the current flowing to the bridge circuit 210 in accordance with the adjustment signal C. The current adjustment circuit 230 decreases the current flowing to the bridge circuit 210 as the magnitude of the adjustment signal C increases, and increases the current flowing to the bridge circuit 210 as the magnitude of the adjustment signal C decreases.

Namely, in the case where the voltage input to the non-inverting input terminal of the operational amplifier 221 is larger than that input to the inverting input terminal of the operational amplifier 221, the current flowing to the bridge circuit 210 is decreased. In contrast, in the case where the voltage input to the non-inverting input terminal of the operational amplifier 221 is smaller than that input to the inverting input terminal of the operational amplifier 221, the current flowing to the bridge circuit 210 is increased.

The current adjustment circuit 230 includes the constant temperature control circuit 231 and a switching circuit 232.

The switching circuit 232 is connected between a power supply line for supplying the drive voltage Vcc to the bridge circuit 210 and a control line CL1 for changing the energization state of the current adjustment circuit 230. The switching circuit 232 includes a transistor which turns on and off in accordance with an operation permission signal S1 from the computation section 30. The switching circuit 232 is configured to output a start signal S11 to the control line CL1 during a predetermined period during which the transistor is on. Notably, the predetermined period during which the transistor is turned on is set in advance not to prevent the output of the adjustment signal C.

The constant temperature control circuit 231 is connected between the power supply line for supplying the drive voltage Vcc and the bridge circuit 210 (specifically, the connection end portion PV). The constant temperature control circuit 231 includes a transistor whose conduction state (on resistance) changes in accordance with the signal flowing through the control line CL1. Specifically, the constant temperature control circuit 231 starts the supply of current to the bridge circuit 210 in accordance with the start signal S11 which is the output of the switching circuit 232. The constant temperature control circuit 231 is configured such that after the supply of current to the bridge circuit 210 is started, the constant temperature control circuit 231 changes the on resistance in accordance with the adjustment signal C, which is the output of the amplification circuit 220. Specifically, when the magnitude of the adjustment signal C increases, the constant temperature control circuit 231 increases the on resistance to thereby decrease the current flowing to the bridge circuit 210. In contrast, when the magnitude of the adjustment signal C decreases, the constant temperature control circuit 231 decreases the on resistance to thereby increase the current flowing to the bridge circuit 210.

In the energization control circuit 21 having the above-described configuration, when the supply of electric current from the DC power supply 40 to the bridge circuit 210 is started, the amplification circuit 220 and the current adjustment circuit 230 perform feedback control for adjusting the current flowing to the bridge circuit 210 such that the potential difference produced between the connection point P+ and the connection point P− becomes zero. As a result, the resistance of the heat generation resistor 15 (in other words, the temperature of the heat generation resistor 15) is controlled to a certain value determined by the variable resistor section 213 (in other words, the first set temperature CH or the second set temperature CL).

Specifically, in the case where the quantity of heat transferred from the heat generation resistor 15 to the combustible gas becomes larger than the quantity of heat generated in the heat generation resistor 15 due to a change in the concentration of the combustible gas contained in the target atmosphere, the temperature of the heat generation resistor 15 decreases and the resistance of the heat generation resistor 15 decreases. In contrast, in the case where the quantity of heat transferred from the heat generation resistor 15 to the combustible gas becomes smaller than the quantity of heat generated in the heat generation resistor 15, the temperature of the heat generation resistor 15 increases and the resistance of the heat generation resistor 15 increases.

When the resistance of the heat generation resistor 15 decreases as described above, the amplification circuit 220 and the current adjustment circuit 230 increase the current flowing to the bridge circuit 210; in other words, the quantity of heat generated in the heat generation resistor 15. In contrast, when the resistance of the heat generation resistor 15 increases, the amplification circuit 220 and the current adjustment circuit 230 decrease the current flowing to the bridge circuit 210; in other words, the quantity of heat generated by the heat generation resistor 15. In this manner, the amplification circuit 220 and the current adjustment circuit 230 perform feedback control such that the resistance of the heat generation resistor 15 (in other words, the temperature of the heat generation resistor 15) approaches a predetermined value.

By measuring the detection signal V1 representing the potential at the connection point P+, the magnitude of the current flowing to the heat generation resistor 15 is found, and the quantity of heat necessary to maintain constant the temperature (in other words, the resistance) of the heat generation resistor 15 is found. Thus, the quantity of heat transferred from the heat generation resistor 15 to the combustible gas (hydrogen gas) is found. Since the quantity of the transferred heat depends on the concentration of the hydrogen gas, the concentration of the hydrogen gas can be determined by measuring the detection signal V1.

1-3. Temperature Adjustment Circuit

Next, the temperature adjustment circuit 25 will be described. The temperature adjustment circuit 25 includes a bridge circuit 250 which is a Wheatstone bridge circuit including the temperature measurement resistor 16, and an amplification circuit 260 which amplifiers a potential difference obtained from the bridge circuit 250.

The bridge circuit 250 is a Wheatstone bridge circuit including the temperature measurement resistor 16, a first bridge fixed resistor 151, a second bridge fixed resistor 152, and a third bridge fixed resistor 153.

The first bridge fixed resistor 151 is connected in series to the temperature measurement resistor 16. Of end portions of the temperature measurement resistor 16, the end portion opposite the end portion connected to the first bridge fixed resistor 151 is grounded. Of end portions of the first bridge fixed resistor 151, the end portion connected to the second bridge fixed resistor 152 is connected to the power supply line for supplying the drive voltage Vcc.

Also, the second bridge fixed resistor 152 is connected in series to the third bridge fixed resistor 153. Of the end portions of the third bridge fixed resistor 153, the end portion opposite the end portion connected to the second bridge fixed resistor 152 is grounded. Of end portions of the second bridge fixed resistor 152, the end portion connected to the first bridge fixed resistor 151 is connected to the power supply line for supplying the drive voltage Vcc.

The connection point P− between the first bridge fixed resistor 151 and the temperature measurement resistor 16 is connected to the inverting input terminal of an operational amplifier 261 through a second temperature adjustment resistor 163. The connection point P+ between the second bridge fixed resistor 152 and the third bridge fixed resistor 153 is connected to the non-inverting input terminal of the operational amplifier 261 through a first temperature adjustment fixed resistor 162. Also, the output of the operational amplifier 261 is supplied to the computation section 30 as a temperature detection signal VT.

The amplification circuit 260 is a differential amplification circuit and includes the operational amplifier 261, the first temperature adjustment fixed resistor 162, the second temperature adjustment resistor 163, a third fixed resistor 164, and a capacitor 265. The first temperature adjustment fixed resistor 162 is connected between the non-inverting input terminal of the operational amplifier 261 and the connection point P+. The second temperature adjustment resistor 163 is connected between the inverting input terminal of the operational amplifier 261 and the connection point P−. The third fixed resistor 164 and the capacitor 265 are connected in parallel between the inverting input terminal of the operational amplifier 261 and the output terminal thereof.

1-4. Computation Section

The computation section 30 computes the concentration of hydrogen gas based on the temperature detection signal VT output from the temperature adjustment circuit 25 and the detection signal V1 output from the energization control circuit 21. The computation section 30 starts upon supply of electric current from the DC power supply 40. After startup, the computation section 30 initializes various sections and starts gas concentration computation processing.

The computation section 30 includes a central processing unit (CPU) for executing various types of computation processing such as the gas concentration computation processing; a storage device such as ROM and RAM which stores various programs, data, etc., which allow the CPU to execute various types of computation processing; an TO port for inputting and outputting various types of signals; a timer for clocking; etc. (not illustrated).

The above-described storage device stores at least temperature conversion data, humidity conversion data, and concentration conversion data.

An example of the temperature conversion data is data which represents the correlation between the environment temperature T of the target atmosphere and the temperature voltage VT (the temperature detection signal VT).

An example of the humidity conversion data is data which represents the correlation between the humidity H within the target atmosphere and the high-temperature-time voltage VH, the low-temperature-time voltage VL, and the temperature voltage.

An example of the concentration conversion data is data which represents the correlation between the high-temperature-time voltage VH or the low-temperature-time voltage VL and the gas concentration X of the combustible gas.

Notably, the present embodiment is configured to use concentration conversion data which represents the correlation between the high-temperature-time voltage VH and the gas concentration X of hydrogen gas. Notably, each conversion data is composed of map data for conversion, a calculation formula for conversion, or the like, and is prepared in advance based on data obtained through an experiment or the like.

The above-mentioned humidity conversion data includes map data for voltage ratio conversion which represents the correlation between the environmental temperature T (the temperature voltage VT) and voltage ratio VC(0) to be described below; and map data for humidity conversion which represents the correlation between voltage ratio difference $\Delta$VC to be described below and the humidity H.

The above-mentioned concentration conversion data includes map data for high-temperature-time voltage conversion which represents the correlation between the temperature voltage VT and high-temperature-time voltage VH(0) to be described below; map data for humidity voltage change conversion which represents the correlation between the high-temperature-time voltage VH and the humidity H, and high-temperature-time voltage change ΔVH(H) to be described below; and map data for gas sensitivity conversion which represents the correlation between the temperature voltage VT and the high-temperature-time voltage VH, and gas sensitivity G(VT) to be described below.

1-5. Method of Detecting Concentration of Hydrogen Gas

Figure 3A:
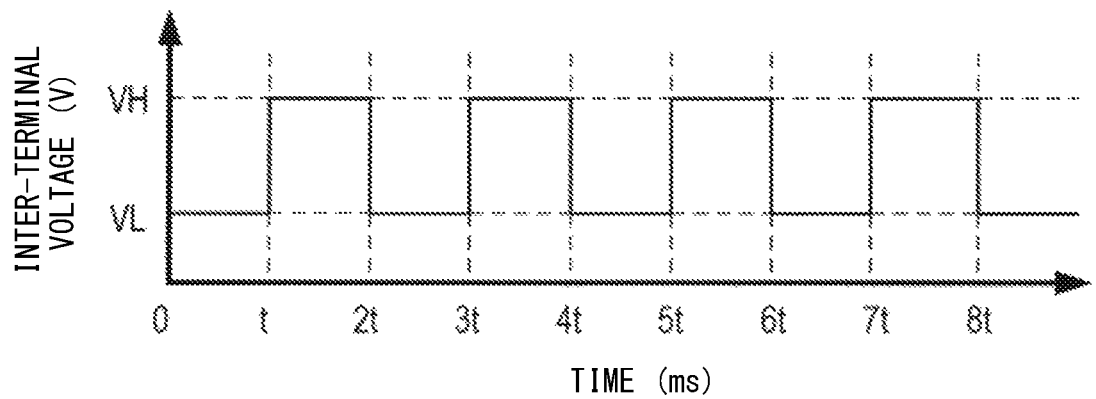
FIG. 3A and FIG. 3B are graphs showing a change in the inter-terminal voltage of a heat generation resistor with time and a change in the temperature of the heat generation resistor with time.
Figure 3B:
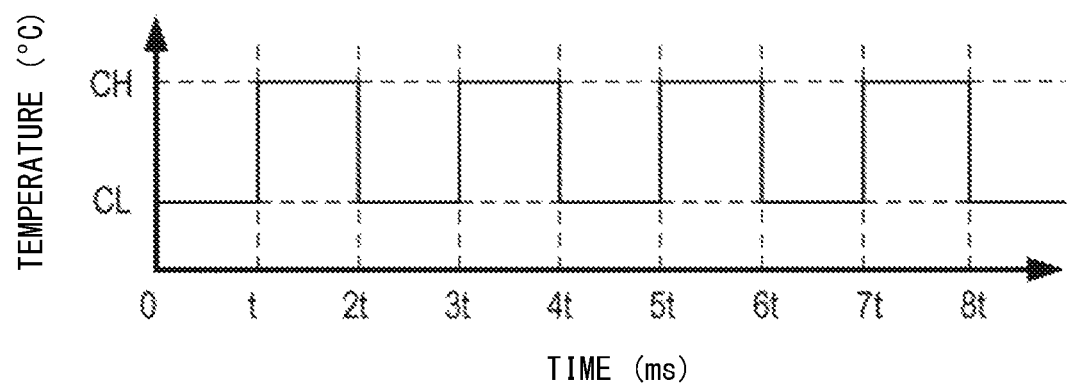

Next, the method of detecting the concentration of hydrogen gas performed by the combustible gas detection apparatus 1 of the present embodiment will be described. When the concentration of hydrogen gas is to be detected, as shown in FIGS. 3A and 3B, the combustible gas detection apparatus 1 alternately and repeatedly performs control processing of holding the set temperature of the heat generation resistor 15 at the low-temperature-side second set temperature CL during a predetermined periodic time t (hereinafter referred to as the "low temperature period t"), and control processing of holding the set temperature of the heat generation resistor 15 at the high-temperature-side first set temperature CH during a predetermined periodic time t (hereinafter referred to as the "high temperature period t").

Specifically, the computation section 30 of the combustible gas detection apparatus 1 outputs the changeover signal CG1 so as to alternately and repeatedly perform control processing of holding the resistance of the bridge circuit 210; i.e., the inter-terminal voltage of the heat generation resistor 15, at the low-temperature-time voltage VL during the low temperature period t and control processing of holding the inter-terminal voltage of the heat generation resistor 15 at the high-temperature-time voltage VH during the high temperature period t.

In the present embodiment, the low temperature period t and the high temperature period t have the same length; specifically, 200 ms. Notably, the total length of one cycle (2t) including the low temperature period t and the high temperature period t is preferably 5 seconds or less. This is because as the length of one cycle increases, the ability of the output to faithfully track an environmental change; in other words, the accuracy of the output, deteriorates.

The computation section 30 executes various types of control processing such as gas concentration computation processing to be executed at the time of gas detection.

The gas concentration computation processing will now be described.

Figure 4A:
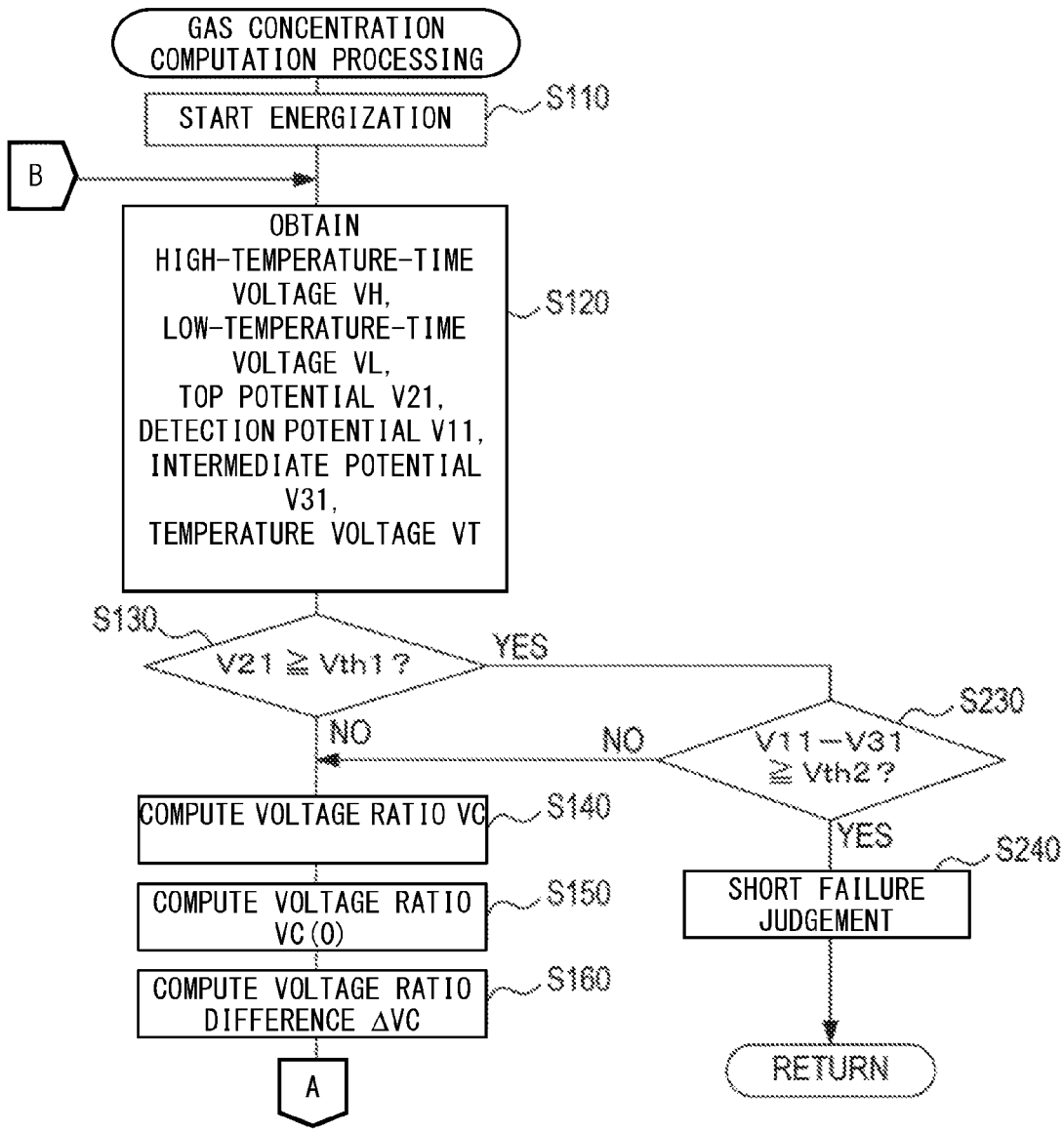
FIG. 4A and FIG. 4B are flowcharts showing the details of gas concentration computation processing.
Figure 4B:
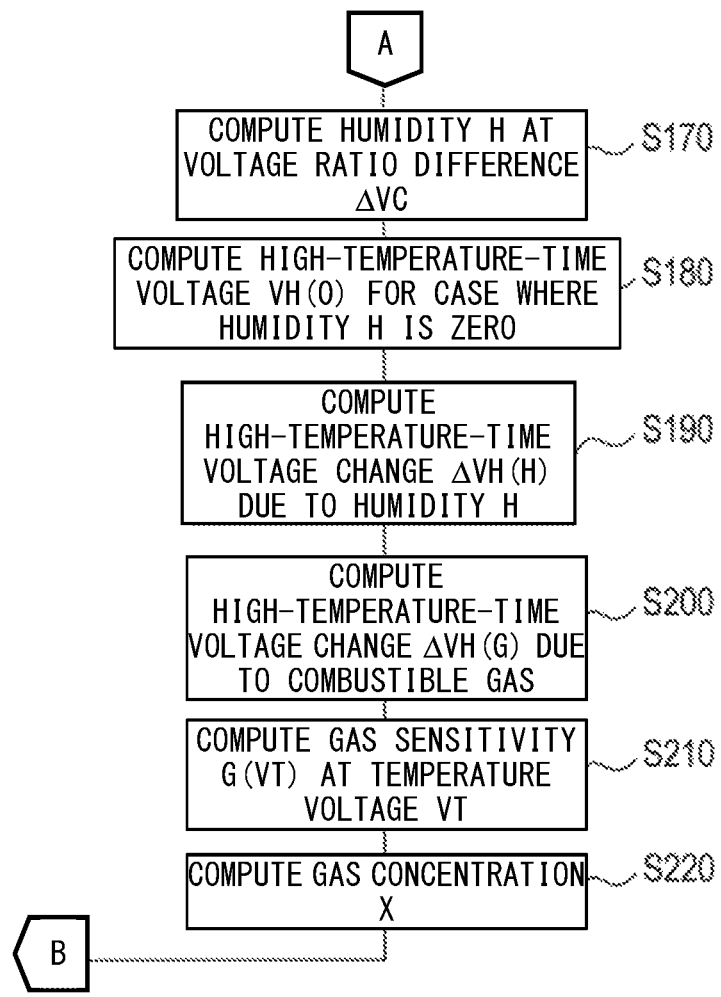

The gas concentration computation processing is control processing which is executed at the time of gas detection by the combustible gas detection apparatus 1 so as to compute the concentration of the combustible gas. Notably, when the combustible gas detection apparatus 1 is started, the computation section 30 starts the gas concentration computation processing. FIGS. 4A and 4B are flowcharts showing the details of the gas concentration computation processing.

When the gas concentration computation processing is started, in S110 (S stands for "step"), the computation section 30 starts the supply of electric current to various portions within the apparatus. Specifically, the computation section 30 starts the supply of electric current to the heat generation resistor 15 by the energization control circuit 21 and the supply of electric current to the temperature measurement resistor 16 by the temperature adjustment circuit 25.

In S120 subsequent thereto, the computation section 30 obtains the low-temperature-time voltage VL, the high-temperature-time voltage VH, a top potential V21, a detection potential V11, an intermediate potential V31 from the energization control circuit 21 and obtains the temperature voltage VT from the temperature adjustment circuit 25.

Notably, the top potential V21 is the potential of the TOP voltage signal V2 detected at that time; the detection potential V11 is the potential of the detection signal V1 detected at that time; the intermediate potential V31 is the potential of the intermediate potential signal V3 detected at that time; and the temperature voltage VT is the voltage of the temperature detection signal VT detected at that time.

In S130 subsequent thereto, the computation section 30 judges whether or not the top potential V21 is equal to or greater than a first judgment value Vth1 determined in advance. In the case where the computation section 30 makes an affirmative judgment, the computation section 30 proceeds to S230. In the case where the computation section 30 makes a negative judgment, the computation section 30 proceeds to S140.

Notably, the first judgment value Vth1 is set in advance based on the potential (potential at the time of maximum energization) produced at the connection end portion PV when the state of control by the amplification circuit 220 and the current adjustment circuit 230 is a state in which the maximum current is supplied from the DC power supply 40 to the bridge circuit 210 (state in which the maximum voltage is applied to the bridge circuit 210). In the present embodiment, a value obtained by subtracting the voltage drop (about 0.6 V) at the constant temperature control circuit 231 from the drive voltage Vcc (5 V) is used as the potential at the time of maximum energization. In the present embodiment, a potential identical to the potential at the time of maximum energization (specifically, 4.4 V) is set as the first judgment value Vth1 in advance.

In the case where the computation section 30 makes an affirmative judgment in S130 and then proceeds to S230, the computation section 30 judges in S230 whether or not the difference D1 (=V11−V31) between the detection potential V11 and the intermediate potential V31 is equal to or greater than a predetermined second judgment value Vth2. In the case where the computation section 30 makes an affirmative judgment, the computation section 30 proceeds to S240. In the case where the computation section 30 makes a negative judgment, the computation section 30 proceeds to S140.

An arbitrary value within the numerical range which ranges from the value of the difference D1 at the time when the constant temperature control circuit 231 is in a short state to the value of the difference D1 at the time when the concentration of hydrogen is high (the resistance of the heat generation resistor 15 has decreased) is set as the second judgment value Vth2 in advance. In the present embodiment, 5.0 mV is set as the second judgment value Vth2.

In the case where the computation section 30 makes an affirmative judgment in S230 and then proceeds to S240, computation section 30 judges in S240 that the bridge circuit 210 is in a short failure state in which it is shorted to the DC power supply 40 (in other words, in the case where a short failure has occurred in the constant temperature control circuit 231). At that time, the computation section 30 changes the state of a short failure flag F1, which is one of the internal flags of the computation section 30, from a reset state to a set state, and reports to an external device (for example, an engine control unit, etc.) connected to the combustible gas detection apparatus 1 that a short failure has occurred.

In the case where the computation section 30 makes a negative judgment in S130 or S230 and then proceeds to S140, in S140, the computation section 30 computes a voltage ratio VC based on the high-temperature-time voltage VH and the low-temperature-time voltage VL. Specifically, the computation section 30 computes the voltage ratio VC using the following [Formula 1].

$$VC = \frac{VH}{VL} \qquad \text{[Formula 1]}$$

In S150 subsequent thereto, based on the temperature voltage VT obtained in S120 and the map data for voltage ratio conversion, the computation section 30 computes a voltage ratio VC(0) corresponding to the environmental temperature T (the temperature voltage VT) for the case where the gas concentration X is zero and the humidity H is zero.

In S160 subsequent thereto, the computation section 30 computes a voltage ratio difference ΔVC corresponding to the environmental temperature T (the temperature voltage VT) while using the voltage ratio VC obtained in S140 and the voltage ratio VC(0) obtained in S150 as input values of [Formula 2].

$$\Delta VC = VC - VC(0) \qquad \text{[Formula 2]}$$

In S170 subsequent thereto, the computation section 30 computes the humidity H corresponding to the voltage ratio difference ΔVC based on the voltage ratio difference ΔVC obtained in S160 and the map data for humidity conversion.

In S180 subsequent thereto, based on the high-temperature-time voltage VH obtained in S120, the temperature voltage VT obtained in S120, and the map data for high-temperature-time voltage conversion, the computation section 30 computes a high-temperature-time voltage VH(0) corresponding to the environmental temperature T (the temperature voltage VT) for the case where the gas concentration X is zero and the humidity H is zero.

In S190 subsequent thereto, based on the high-temperature-time voltage VH obtained in S120, the humidity H obtained in S170, and the map data for humidity voltage change conversion, the computation section 30 computes a high-temperature-time voltage change ΔVH(H) which represents a voltage change of the high-temperature-time voltage VH due to the humidity H.

In S200 subsequent thereto, the computation section 30 computes a high-temperature-time voltage change ΔVH(G) which represents a voltage change of the high-temperature-time voltage VH due to the combustible gas while using the high-temperature-time voltage VH obtained in S120, the high-temperature-time voltage VH(0) obtained in S180, and the high-temperature-time voltage change ΔVH(H) obtained in S190 as input values of [Formula 3].

$$\Delta VH(G) = VH - VH(0) - \Delta VH(H) \qquad \text{[Formula 3]}$$

In S210 subsequent thereto, the computation section 30 computes a gas sensitivity G(VT) which represents the sensitivity to the combustible gas after correction (the unit is the reciprocal of the gas concentration X) based on the high-temperature-time voltage VH obtained in S120, the temperature voltage VT obtained in S120, and the map data for gas sensitivity conversion.

In S220 subsequent thereto, the computation section 30 computes the gas concentration X of the combustible gas (hydrogen) while using the high-temperature-time voltage change ΔVH(G) calculated in S200 and the gas sensitivity G(VT) calculated in S210 as input values of [Formula 4].

$$X = \frac{\Delta VH(G)}{G(VT)} \qquad \text{[Formula 4]}$$

After completion of S220, the computation section 30 again proceeds to S120 and repeatedly executes the above-described processing.

As described above, in the gas concentration computation processing, the computation section 30 computes the gas concentration X (hydrogen concentration) by the processing of S120 and S140 to S220. Also, in the gas concentration computation processing, before computation of the gas concentration, the computation section 30 performs the judgment processing in S130 and S230 so as to judge based on the top potential V21 and the difference D1 (=V11−V31) whether or not the bridge circuit 210 is in a short failure state in which it is shorted to the DC power supply 40 (in other words, in the case where a short failure has occurred in the constant temperature control circuit 231).

In the case where the computation section 30 determines in the gas concentration computation processing that a short failure has occurred, the computation section 30 determines that a short failure has occurred without computing the gas concentration X (S240). In the case where the computation section 30 determines in the gas concentration computation processing that no short failure has occurred, the computation section 30 computes the gas concentration X.

1-6. Judgment of Failure of Temperature Control Circuit

In the combustible gas detection apparatus 1, when the bridge circuit 210 is in a short failure state in which it is shorted to the DC power supply 40 (in other words, in the case where a short failure has occurred in the constant temperature control circuit 231), the output voltage of the DC power supply 40 (the drive voltage Vcc) is applied directly to the bridge circuit 210. When the application of such a voltage to the heat generation resistor 15 continues, the temperature of the heat generation resistor 15 increases, and the resistance of the heat generation resistor 15 increases, whereby the voltage between the opposite ends of the heat generation resistor 15 increases. Notably, the first bridge fixed resistor 111, the second bridge fixed resistor 112, and the variable resistor section 213, which are provided as reference resistors of the bridge circuit 210, exhibit a lower resistance change with temperature change as compared with the heat generation resistor 15. Therefore, when the voltage between opposite ends of the heat generation resistor 15 increases, the potential at the connection point P+ between the first bridge fixed resistor 111 and the heat generation resistor 15 is more apt to be higher than that at the connection point P− between the second bridge fixed resistor 112 and the variable resistor section 213.

Meanwhile, in the combustible gas detection apparatus 1, when a state in which the resistance of the heat generation resistor 15 decreases due to the combustible gas (hydrogen) to be detected continues, in order to increase the resistance of the heat generation resistor 15, the amplification circuit 220 and the current adjustment circuit 230 control the state of supply of electric current from the DC power supply 40 to the bridge circuit 210 so that the maximum current is supplied to the bridge circuit 210 (or the maximum voltage is applied to the bridge circuit 210). At that time, since the resistance of the heat generation resistor 15 decreases due to the combustible gas (hydrogen) to be detected, the voltage between opposite ends of the heat generation resistor 15 decreases. As a result of the decrease in voltage between the opposite ends of the heat generation resistor 15, the potential at the connection point P+ between the first bridge fixed resistor 111 and the heat generation resistor 15 is more apt to be lower than that at the connection point P− between the second bridge fixed resistor 112 and the variable resistor section 213.

Therefore, the difference D1 (=V11−V31) obtained by subtracting the intermediate potential V31 (the potential at the connection point P−) from the detection potential V11 (the potential at the connection point P+) assumes different values between the "state in which the bridge circuit 210 is in a short failure state in which it is shorted to the DC power supply 40 (in other words, in the case where the constant temperature control circuit 231 is in a short failure state)" and the "state in which the resistance of the heat generation resistor 15 decreases due to the combustible gas (hydrogen)."

Also, as described above, an arbitrary value within the numerical range which ranges from the value of the difference D1 at the time when the bridge circuit 210 is in a short failure state in which it is shorted to the DC power supply 40 (in other words, in the case where the constant temperature control circuit 231 is in a short state) to the value of the difference D1 at the time when the concentration of hydrogen is high (in the case where the resistance of the heat generation resistor 15 has decreased) is set as the second judgment value Vth2 in advance. In the present embodiment, 5.0 mV is set as the second judgment value Vth2.

Therefore, by using the result of comparison between the difference D1 and the second judgment value Vth2, it becomes possible to distinguish the "state in which the bridge circuit 210 is in a short failure state in which it is shorted to the DC power supply 40 (in other words, in the case where the constant temperature control circuit 231 is in a short failure state)" from the "state in which the resistance of the heat generation resistor 15 decreases due to the combustible gas (hydrogen)."

Notably, the difference D1 (=V11−V31) obtained by subtracting the intermediate potential V31 from the detection potential V11 changes even when the constant temperature control circuit 231 is normal. Therefore, in addition to the difference D1, the top potential V21 is used for making the judgment. Thus, it is possible to judge whether or not the constant temperature control circuit 231 is in a short failure state.

Therefore, by executing the judgment processing of S130 and S230 in the gas concentration computation processing, the computation section 30 can judge based on the top potential V21 and the difference D1 (=V11−V31) whether or not the bridge circuit 210 is in a short failure state in which it is shorted to the DC power supply 40 (in other words, in the case where a short failure has occurred in the constant temperature control circuit 231).

1-7. Effects

As described above, the combustible gas detection apparatus 1 of the present embodiment is configured such that, in the gas concentration computation processing, it judges, based on the result of the comparison between the top potential V21 and the first judgment value Vth1 (S130) and the result of the comparison between the difference D1 (=V11−V31) and the second judgment value Vth2 (S230), whether or not the bridge circuit 210 is in a short failure state in which it is shorted to the DC power supply 40 (in other words, in the case of a failure (specifically, a short failure) of the constant temperature control circuit 231).

Specifically, in the case where the top potential V21 is equal to or greater than the first judgment value Vth1 (in the case where an affirmative judgment is made in S130) and the difference D1 (=V11−V31) is equal to or greater than the second judgment value Vth2 (in the case where an affirmative judgment is made in S230), the combustible gas detection apparatus 1 judges that the bridge circuit 210 is in a short failure state in which it is shorted to the DC power supply 40 (in other words, in the case where a short failure has occurred in the constant temperature control circuit 231) (S240).

As described above, the difference D1 (=V11−V31) obtained by subtracting the intermediate potential V31 from the detection potential V11 assumes different values between the "state in which the bridge circuit 210 is in a short failure state in which it is shorted to the DC power supply 40 (in other words, in the case where the constant temperature control circuit 231 is in a short failure state)" and the "state in which the resistance of the heat generation resistor 15 decreases due to the combustible gas (hydrogen)." Therefore, when the second judgment value Vth2 is set in the above-described manner and the result of the comparison between the difference D1 and the second judgment value Vth2 is used, it becomes possible to distinguish the "state in which the bridge circuit 210 is in a short failure state in which it is shorted to the DC power supply 40 (in other words, in the case where the constant temperature control circuit 231 is in a short failure state)" from the "state in which the resistance of the heat generation resistor 15 decreases due to the combustible gas (hydrogen)."

Notably, the difference D1 (=V11−V31) changes even when the constant temperature control circuit 231 is normal. Therefore, by performing the judgment using the top potential V21 in addition to the difference D1, it is possible to judge whether or not the bridge circuit 210 is in a short failure state in which it is shorted to the DC power supply 40 (in other words, in the case where the constant temperature control circuit 231 is in the short failure state).

Therefore, by executing the judgment processing of S130 and S230 in the gas concentration computation processing, the combustible gas detection apparatus 1 can distinguish the "state in which the bridge circuit 210 is in a short failure state in which it is shorted to the DC power supply 40 (in other words, in the case where the constant temperature control circuit 231 is in a short failure state)" from the "state in which the resistance of the heat generation resistor 15 decreases due to the combustible gas (hydrogen)" based on the top potential V21 and the difference D1.

Accordingly, when the bridge circuit 210 is in a short failure state in which it is shorted to the DC power supply 40 (in other words, in the case where a short failure has occurred in the constant temperature control circuit 231 which controls the current supplied to the bridge circuit 210), the combustible gas detection apparatus 1 can detect the short failure.

Notably, in the case where the top potential V21 is judged not to be equal to or greater than the first judgment value Vth1 (in the case where a negative judgment is made in S130) or the difference D1 is judged not to be equal to or greater than the second judgment value Vth2 (in the case where a negative judgment is made in S230), the combustible gas detection apparatus 1 can compute the gas concentration X by the processing in S120 and S140 to S220, whereby the hydrogen concentration can be detected.

1-8. Correspondence Between Embodiment and Claims

The following is a description of the correspondence between terms used in claims appended hereto and terms used in the present embodiment.

The combustible gas detection apparatus 1 corresponds to the fluid state detection apparatus; the heat generation resistor 15 corresponds to the heat generation resistor; the bridge circuit 210 corresponds to the Wheatstone bridge circuit; the amplification circuit 220 and the current adjustment circuit 230 correspond to the bridge control section; and the computation section 30 which executes S120 and S140 to S220 in the gas concentration computation processing corresponds to the computation section.

The first bridge fixed resistor 111 corresponds to the first resistor section; the second bridge fixed resistor 112 corresponds to the second resistor section; and the variable resistor section 213 corresponds to the third resistor section. The operational amplifier 221 corresponds to the operational amplifier. The constant temperature control circuit 231 corresponds to the energization control section, and the DC power supply 40 corresponds to the power supply apparatus.

The end portion PG at which the heat generation resistor 15 and the variable resistor section 213 are connected together corresponds to the reference point; and the connection end portion PV at which the first bridge fixed resistor 111 and the second bridge fixed resistor 112 are connected together corresponds to the high potential point. The connection point P+ at which the first bridge fixed resistor 111 and the heat generation resistor 15 are connected together corresponds to the first potential point; and the connection point P− at which the second bridge fixed resistor 112 and the variable resistor section 213 are connected together corresponds to the second potential point.

The computation section 30 which executes S130, S230, and S240 in the gas concentration computation processing corresponds to the failure judgment section; the first judgment value Vth1 corresponds to the voltage upper limit judgment value; and the second judgment value Vth2 corresponds to the failure judgment value.

2. Other Embodiments

Although an embodiment of the present invention has been described, the present invention is not limited thereto and can be implemented in various forms without departing from the scope of the invention.

For example, the first judgment value Vth1 and the second judgment value Vth2 are not limited to the above-described numerical values and may be arbitrarily set so long as the first judgment value Vth1 and the second judgment value Vth2 make it possible to distinguish the "state in which the bridge circuit 210 is in a short failure state in which it is shorted to the DC power supply 40 (in other words, in the case where the constant temperature control circuit 231 is in a short failure state)" from the "state in which the resistance of the heat generation resistor 15 decreases due to the combustible gas (hydrogen)."

Also, the gas concentration computation processing may be modified such that, after making a negative judgment in S230, the computation section 30 executes a step (resistance decrease judgment step) of judging whether or not the hydrogen concentration is high (whether the resistance of the heat generation resistor 15 has decreased) is executed, and then proceeds to S140. In this case, in the resistance decrease judgment step, the computation section 30 may change the state of the hydrogen concentration high flag (or a resistance decrease flag), which is one of the internal flags of the computation section 30, from a reset state to a set state. Also, in the resistance decrease judgment step, the computation section 30 may report to an external device (for example, an engine control unit, etc.) connected to the combustible gas detection apparatus 1 that the hydrogen concentration is high (in the case where the resistance of the heat generation resistor 15 has decreased).

Also, in the above-described embodiment, the concentration of the combustible gas is detected as a fluid state. However, the fluid state is not limited thereto, and the flow rate of gas, the flow rate of liquid, or the like may be detected.

The invention has been described in detail with reference to the above embodiments. However, the invention should not be construed as being limited thereto. It should further be apparent to those skilled in the art that various changes in form and detail of the invention as shown and described above may be made. It is intended that such changes be included within the spirit and scope of the claims appended hereto.

This application is based on Japanese Patent Application No. 2015-079442 filed Apr. 8, 2015, incorporated herein by reference in its entirety.

What is claimed is:

1. A fluid state detection apparatus comprising:
a heat generation resistor which is disposed in a target atmosphere and whose resistance changes in accordance with a fluid state to be detected;
a Wheatstone bridge circuit configured by connecting, in parallel a first side and a second side, the first side including the heat generation resistor and a first resistor section connected in series, and the second side including a second resistor section and a third resistor section connected in series;
a bridge control section which controls the state of supply of electric current from a power supply to the Wheatstone bridge circuit; and
a computation section which computes the fluid state within the target atmosphere from a resistance of the heat generation resistor, wherein
the bridge control section includes an operational amplifier having an output terminal and two input terminals and an energization control section which controls a state of supply of electric current to the Wheatstone bridge circuit in accordance with the output of the operational amplifier such that a potential difference between the two input terminals of the operational amplifier becomes zero;
the Wheatstone bridge circuit is configured such that one of connection points where the first side and the second side are connected together serves as a reference point connected to one side of the bridge control section and becomes a low potential side when the bridge control section applies a voltage to the Wheatstone bridge circuit, and another one of the connection points where the first side and the second side are connected together serves as a high potential point connected to the other side of the bridge control section and becomes a high potential side when the bridge control section applies the voltage to the Wheatstone bridge circuit, a connection point where the first resistor section and the heat generation resistor are connected together serves as a first potential point connected to one input terminal of the operational amplifier, and a connection point where the second resistor section and the third resistor section are connected together serves as a second potential point connected to the other input terminal of the operational amplifier; and the fluid state detection apparatus includes a failure judgment section which compares a potential at the high potential point with a predetermined voltage upper limit judgment value and compares a difference obtained by subtracting a potential at the second potential point from a potential at the first potential point with a predetermined failure judgment value so as to judge that the Wheatstone bridge circuit is in a short failure state in which the bridge circuit is shorted to the power supply when the potential at the high potential point is equal to or greater than the voltage upper limit judgment value and the difference is equal to or greater than the failure judgment value.

2. The fluid state detection apparatus as claimed in claim 1, wherein the computation section computes hydrogen gas concentration as the fluid state.

3. The fluid state detection apparatus as claimed in claim 1, wherein the power supply is integrated into the fluid state detection apparatus.

4. The fluid state detection apparatus as claimed in claim 2, wherein the power supply is integrated into the fluid state detection apparatus.

* * * * *